United States Patent
Volkov et al.

[11] 3,976,061
[45] Aug. 24, 1976

[54] APPARATUS FOR SURGICAL TREATMENT OF BONES AND JOINTS

[76] Inventors: Mstislav Vasilievich Volkov, 1, Stroitelnaya ulitsa, 6, korpus 1, kv. 63; Oganes Vardanovich Oganesian, ulitsa Pervomaiskaya, 74, kv. 87, both of Moscow, U.S.S.R.

[22] Filed: June 11, 1975

[21] Appl. No.: 586,137

[30] Foreign Application Priority Data
July 22, 1974 U.S.S.R............................ 2052127

[52] U.S. Cl. ..................... 128/84 B; 128/92 A
[51] Int. Cl.² .................................. A61F 5/04
[58] Field of Search ............. 128/84 R, 84 B, 84 C, 128/87, 83, 92 R, 92 A, 92 B, 92 E

[56] References Cited
UNITED STATES PATENTS

| | | | |
|---|---|---|---|
| 2,120,446 | 6/1938 | Thomas | 128/84 B |
| 2,406,987 | 9/1946 | Anderson | 128/92 A |
| 2,687,720 | 8/1954 | Haboush | 128/84 R |
| 3,727,610 | 4/1973 | Riniker | 128/92 A |

FOREIGN PATENTS OR APPLICATIONS

| | | | |
|---|---|---|---|
| 227,511 | 1/1970 | U.S.S.R. | 128/92 A |

*Primary Examiner*—John D. Yasko
*Attorney, Agent, or Firm*—Steinberg and Blake

[57] ABSTRACT

The proposed apparatus for surgical treatment of bones and joints comprises at least two pairs of needles designed to be driven through the juxtaposed bones. The tips of the needles of each pair are secured in at least one brace so that each pair of needles forms a rigid system with the brace, said rigid system being secured on the respective bone being juxtaposed. Said rigid systems are interconnected by two distractors each of which is formed as a split member carrying, in the midportion thereof, a system of two guides with two sliders attached to the respective components of the distractors, said guides being perpendicular to each other and also to the longitudinal axes of the distractor components associated therewith, and the sliders are provided with screw actuators serving to propel said sliders along said guides. The apparatus permits correcting lateral and rotary displacements of the juxtaposed bones, ensuring secure fixation thereof in the compression or distraction position.

5 Claims, 11 Drawing Figures

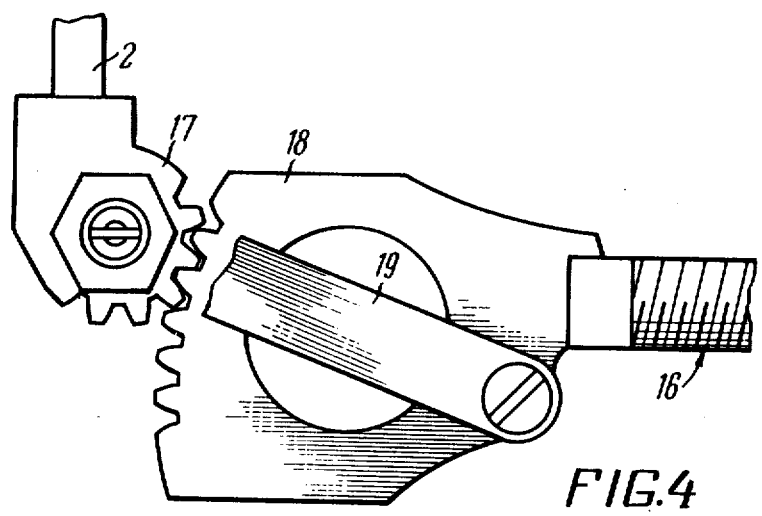
FIG.4
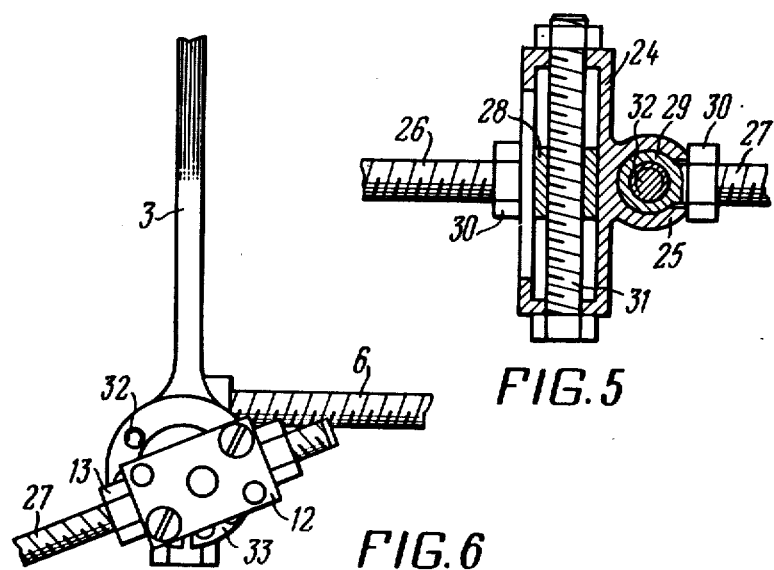
FIG.5
FIG.6

APPARATUS FOR SURGICAL TREATMENT OF BONES AND JOINTS

The present invention relates to medical equipment and, more particularly, to apparatus for surgical treatment of bones and joints. The apparatus of this invention may find application in orthopaedics and traumatology for correcting recent uncorrected and inveterate joint dislocations followed by the restitution of joint movement; for restoring the functions of the joints in the post-arthroplasty period; for eliminating joint cont contracture; for fixing periarticular and diaphyseal fractures and pseudoarthroses in the compression or distraction position and simultaneously restoring the mobility of the nearest joint; for elongating shortened bones without interfering with the mobility of the nearest joint; and for effecting compression arthrodesis with any functionally desirable angle of fixation of the joint ends.

It is widely known in the art to employ apparatus for surgical treatment of bones and joints which comprise at least two pairs of needles. The tips of the needles of each pair are secured in one brace or in two rigidly interconnected braces, so that each pair of needles forms a rigid system with the brace(s). The needles or each rigid system are driven through one of the bones being juxtaposed. Said rigid system are interconnected with the aid of distractors which enable the distance between the systems to be varied. Should the apparatus be used to treat bone fractures, the distractors are rigidly fastened to the braces, whereas, employed for treating joints, the distractors are fixed to one rigid system of needles and braces and connected to the other rigid system by way of an articulated joint simulating the movements of the actual joint. Thus, a known apparatus for surgical treatment of joint disaeses and injuries (see: USSR Inventors's Certificate No. 306,842) comprises two braces at the feet whereof there are disposed self-adjusting cylinders with nipples serving to tighten a pair of needles with threaded tips. One brace of said known apparatus, which for the sake of convenience may be regarded as an axial one, serves to fix e.g. the distal end of the humeral bone, the fixation being achieved with the aid of an axial needle driven through the pivotal axis of the joint and a locking needle driven through the joint end through which passes the pivotal axis of the joint. The other brace of the apparatus, termed rotary, fixes, with the aid of the other pair of needles, the other joint end, in this case for fixing the proximal end of the ulna. The two braces are interconnected by means of distractors.

The elbow-, ankle- and radio-carpal joints are treated by means of distractors which are secured to the feed of the axial brace with the aid or uni-axial link whose axis is aligned with the longitudinal axis of the axial needle. At the other end, the distractors are fixed to the fixed brace. The distractors are formed as split members connected by split nuts whereby the distance between the distractor-connected braces may be varied.

The distractors employed in the prior art apparatus for treatment of the knee joint are provided with an articulation arrangement formed as a gear wheel fixed on the axial needle of the axial brace, the latter being mounted on the distal end of the femur which cooperates with a gear quadrant rigidly coupled with the rotary brace. The gear wheel is connected with the gear quadrant by means of two connecting rods.

The braces of the apparatus are interconnected at the top with the aid of a bending-unbending device which provides for a gradual and measured rotation of one rigid system of braces and needles with respect to the other and thereby of the joint ends.

Application of the foregoing apparatus starts by driving the axial needle of the apparatus along the pivotal axis of the joint normally to the main plane of joint rotation, i.e. through the centre of the numeral pulley or through the fulcrum of the wrist bones, or through the center of the astragalus, When the apparatus is applied to the knee joint, the axial needle passes in the main plane of motion of the joint and through those points of the femoral joint end which describe the least curve in the course of flexion and extension. After the axial needle has been passed, the locking needle of the pair is placed in position in keeping with its arrangement in the apparatus. Then the other two needles are passed through the other joint end, whereupon the apparatus is applied and all the needles are fixed and tensioned in the braces thereof.

After the apparatus has been applied, the joint ends are spaced by a desired distance with the aid of the split nuts of the distractors, and, using the bending-unbending device of the apparatus, the latter is subjected to gradual and measured bending and unbending, thereby restituting the mobility of the joint.

However, the prior art apparatus cannot be used to reposition the joint ends in cases of dislocation, keeping the joint ends precisely aligned while restoring the function of the joint; nor can it be employed for repositioning the bone fragments in cases of fractures, keeping them precisely aligned in the compression or distraction position. The reason for this disadvantage consists in that the two rigid systems of braces and needles with the bones secured therein cannot execute a relative motion in the frontal and sagittal planes of the human body, making it impossible to correct a lalateral displacement of the bones to be juxtaposed. Furthermore, the prior art apparatus cannot be employed to correct rotary displacements of the bones to be juxtaposed.

It is an object of the present invention to provide an apparatus for surgical treatment of bones and joints enabling lateral displacements of the bones being juxtaposed to be corrected.

It is another object of the present invention to provide an apparatus for surgical treatment of bones and joints enabling rotary displacements of the bones being juxtaposed to be corrected.

It is a further object of the present invention to provide an apparatus for surgical treatment of bones and joints which would be simple in design and convenient to handle.

The foregoing objects are attained in an apparatus for surgical treatment of bones and joints, comprising at least two pairs of needles to be driven through the bones being juxtaposed, the tips of the needles of each pair being secured in at least one brace so that each pair of needles and the brace define a rigid system to be fixed on the respective bone being juxtaposed, and also comprising distractois interconnecting said rigid systems, wherein, in accordance with the invention, each of the distractors is formed as a split member carrying in the midportion thereof, a system of two guides with two sliders attached to the respective ends of the distractors, the guides being perpendicular to each other and to the longitudinal axes of the distractor components with which the guides are connected and the sliders being provided with screw actuators propelling the former along the guides.

The sliders and the guides are preferably round in cross-section and thereby capable of executing a rotary motion relative to each other.

The distractors are desirably so attached to the braces of said rigid systems as to be able to execute a fixed turn about their axes.

The proposed apparatus for surgical treatment of bones and joints is simpler in design, more convenient in handling and has a wider functional scope than the prior art apparatus.

The chief advantage of the proposed apparatus consists in its repositioning devices, i.e. the guides with the sliders, which permit a gradual and measured reduction of the dislocated joint ends keeping them precisely aligned under both static and dynamic conditions, as well as repositioning and secure fixation of the fracture bone fragments, said repositioning devices being disposed on the distractors, thereby facilitating the handling of the apparatus. With one pair of distractors, use can be made of braces simple in design and varying in size depending on the particular segment of the extremety.

The proposed apparatus is more maneuverable and functionally versatile than the prior art apparatus; it assures complete static and dynamic unloading of the joint, simultaneously ensuring precise alignment of the joint ends as well as active and passive movements in the joint unloaded by the apparatus.

The proposed apparatus provides for spatially rigid fixation of the joint ends and for the reproduction of joint movement, keeping the joint ends spaced permanently apart by a predetemined distance, which obviates friction of the joint surfaces and prevents reflex contracture of the muscles.

After the ankylosed joints have been mobilized, the proposed apparatus eliminates excess mobility of the joint, provides for precise alignment of the joint ends and enables joint surfaces to be formed correctly.

The apparatus of this invention permits gradually and proportionately eliminating joint contracture in the entire amplitude of motion and restoring its function. In the course of contracture correction, the contracture-eliminating effort is correctly distributed between the joint ends in keeping with the biomechanical characteristics of each individual joint.

In the cases of inveterate dislocations, the apparatus of the invention permits of a gradual and measured closed reduction of the dislocated joint ends, after which the joint movement is restituted and its function restored, with the joint ends kept in precise alignment.

In cases of periarticular fractures and false joints, the proposed apparatus not only completely unloads the nearby joint and restores its movement, but also ensures spatially rigid fixation of the bone fragments pressed one against the other, which brings about their union in a short time.

In patients with osteal ankyloses of the ankle- and knee joints with partially united joint ends in an aberrant position of the extremety and with the muscles pathologically altered, preventing restitution of the joint function, the apparatus permits gradually correcting the aberrant position of the extremety in a closed manner followed by compression arthodesis.

The invention will be further understood from the following description of exemplary embodiments thereof taken in conjunction with the accompanying drawings, wherein:

FIG. 4 is a view of a gear wheel and a gear quadrant taken along the arrow IV in FIG. 3;

FIG. 5 is a longitudinal sectional view of guides with sliders, in accordance with the invention;

FIG. 6 is a view of a brace taken along the arrow VI in FIG. 2;

The invention will be further undrstood from the following description of exemplary embodiments thereof taken in conjunction with the accompanying drawings.

Figure 1:
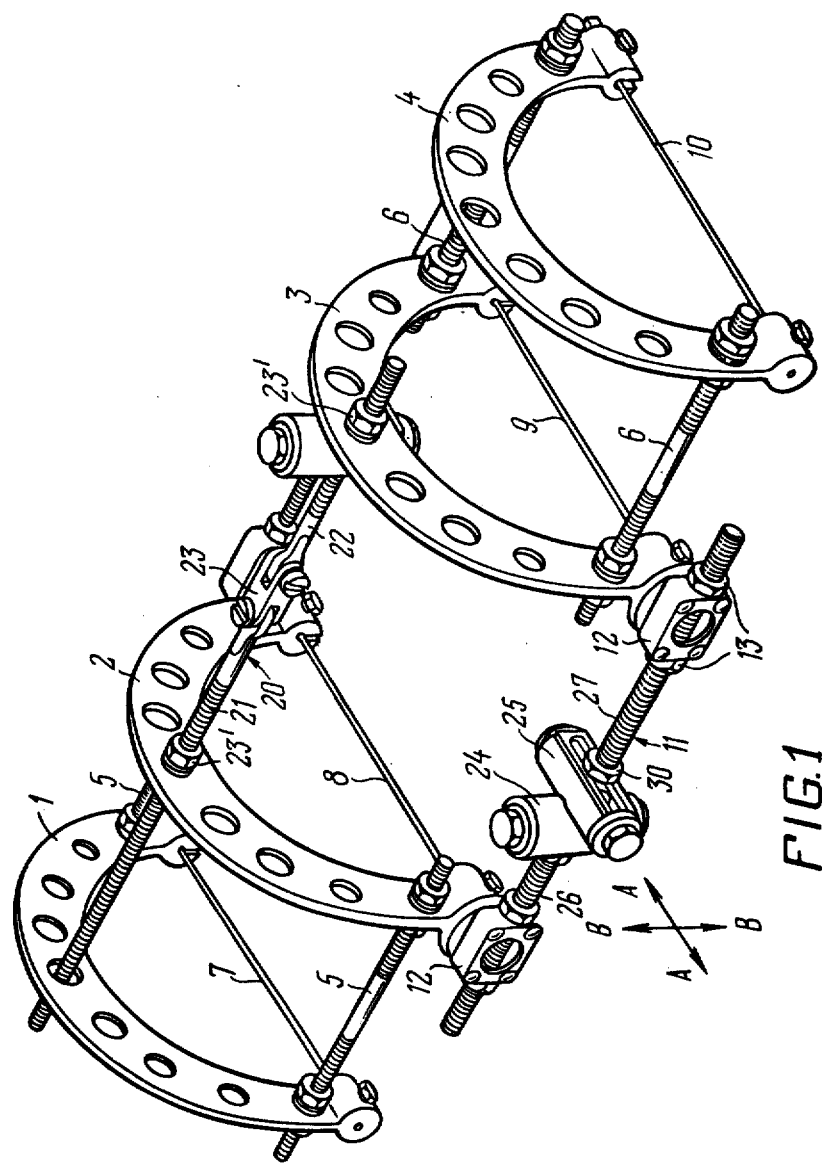
FIG. 1 is a general schematic view of an apparatus with distractors for surgical treatment of bones, in accordance with the invention.

Referring now to the drawings, the proposed apparatus for surgical treatment of bones and joints comprises four braces 1, 2, 3 and 4 (FIG. 1). The braces 1 and 2 are rigidly interconnected by two tie bolts 5, while the braces 3 and 4 by two tie bolts 6. Needles 7, 8, 9 and 10 are secured by way of the tips thereof in the braces 1, 2, 3 and 4, respectively. The needles 7 and 8 and the braces 1 and 2 form one rigid system, while the needle 9 and 10 and the braces 3 and 4 form a second rigid system, the two rigid systems being interconnected by two distractors 11. In order that the spacing of the rigid systems may be varied, the distractors are provided with a screw thread and are fastened to boxes 12 which are screwed on the braces 2 and 3 by means of split nuts 13; in the apparatus for fixing bone fragments in fractures, shown in FIG. 1, both ends of the distractor 11 are fastened to the rigid systems by means of the split nuts 13, whereas, if the apparatus is employed for joint therapy, one end of the distractor is secured with the aid of the split nuts 13 while the other by means of an articulated link simulating the joint movement. Thus, in the apparatus employed for treating the elbow-, ankle- and radio-carpal joints, illustrated in FIG. 2, distractor 14 is fastened to the brace 2 by means of a bearing 15 mounted on the brace 2 coaxially with the needle 8 which is to be driven through the joint pivot. In the apparatus for treating the knee joint, shown in FIG. 3, distractor 16 is fastened to the brace 2 by means of a polycentric mechanism comprising a gear wheel 17 (FIGS. 3 and 4) mounted on the brace 2 coaxially with the needle 8 FIG. 3) and cooperating with a gear quadrant 18 (FIGS. 3 and 4) to which the end of the distractor 16 is secured. The gear quadrant 18 is coupled with the gear wheel 17 with the aid of two connecting rods 19.

The braces 2 and 3 are interconnected at the top (FIGS. 1, 2 and 3) by a bending-unbending arrangement 20 constituted by two rods 21 and 22 fastened together by a universal joint 23. The position of the bending-unbending arrangement 20 is fixed with the aid of nuts 23¹. The bending-unbending arrangment 20 serves for the restitution of the flexion and extension functions when the apparatus is employed for joint therapy. If the apparatus is used to treat fractures, the bending-unbending arrangment 20 is instrumental in eliminating angular displacements of the bone fragments in the sagittal plane of the body.

Each of the distractors 11 (FIG. 1), 14 (FIG. 2) and 16 (FIG. 3) is formed as a split member carrying, in the midportion thereof, a system of two guides 24 and 25. The guides 24 and 25 are perpendicular to each other and to the longitudinal axes of distractor components 26 and 27 with which they are connected. A slider 28 (FIG. 5) coupled with the distractor components 26 moves along the guide 24, while a slider 29 coupled with the distractor component 27 moves along the guide 25.

The distractor components 26 and 27 are provided with a screw thread cooperating with nuts 30 locking the sliders 28 and 29 relative to the guides 24 and 25, respectively.

The slider 28 is propelled by a screw actuator formed as a drive screw 31 which cooperates with the screw thread formed in the slider 28. Similarly, the slider 29 is propelled by a drive screw 32. The drive screws 31 and 32 make it possible to displace one rigid system composed of the needles 7 and 8 (FIG. 1) and the braces 1 and 2 with respect to the other rigid system composed of the needles 9 and 10 and the braces 3 and 4 in two mutually perpendicular directions A-A and B-B in the brace plane, as shown in the drawing by arrows. In order that the position of the guides 24 and 25 may be changed in the plane of the braces 1, 2, 3 and 4, the distractors 11 are so secured to the braces 2 and 3 as to be able to execute a fixed turn about the axes thereof. To this end, there are provided the split nuts 13 cooperating with the screw thread on the ends of the distractor 11.

When the apparatus is employed for treating the elbow joint, the component 27 of the distractor 14 (FIG. 2) which is fixed to the brace 3 must be positioned at an angle to the screws 6. To this end, the brace 3 is provided with flanges 33 having threaded holes 34 arranged circumferentially (FIG. 6) whereby the boxes 12 can be attached to the flanges 33, and hence the distractors 44 can be positioned at various angles to the screws 6 in accordance with the positioning of the elbow joint ends. When the apparatus is used for treating other joints, the end of the distractor is fastened to the brace 3 in parallelism with the screws 6.

Figure 2:
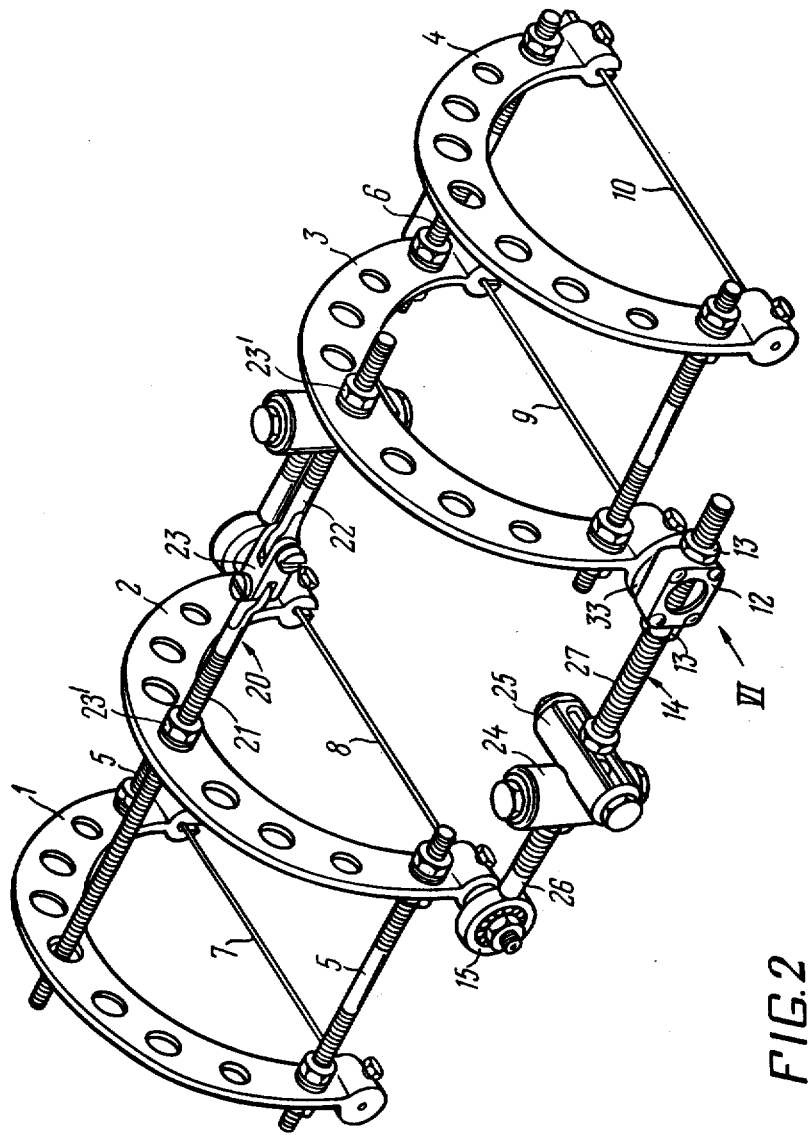
FIG. 2 is a general view of an apparatus with distractors for surgical treatment of the elbow-, ankle- and radio-carpal joints, in accordance with the invention.

Besides, when the apparatus shown in FIG. 2 is employed for treating the elbow joint, the brace 3 must be inclinded towards the brace 1 and mounted at an angle of approximately 30° with respect to the tie bolts 5 (not shown). This arrangement is needed lest the brace 2 should come to be abutted against the brace 3 as the joint fixed in the apparatus undergoes fully extension.

Figure 7:
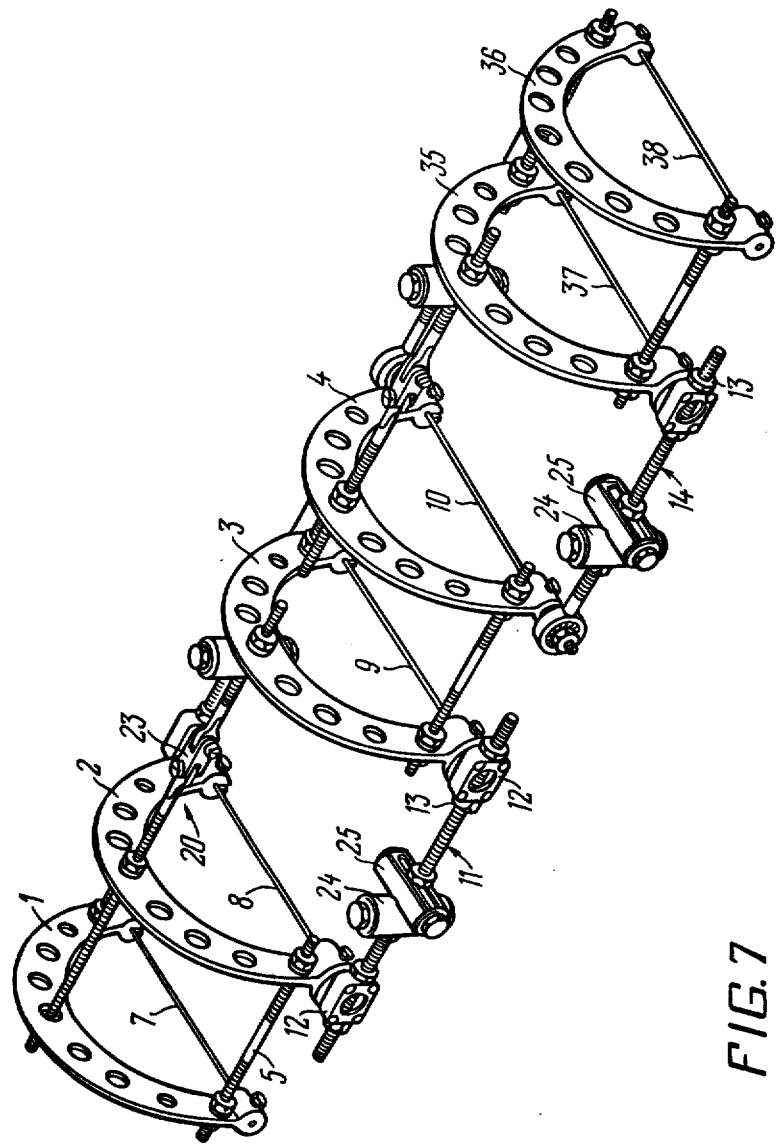
FIG. 7 is a general view of an apparatus for surgical therapy of fractures and dislocations, in accordance with the invention.

In cases of fracture dislocations, to permit simultaneously repositioning the joint ends and the bone fragments, another two braces 35 and 36 (FIG. 7) with needles 37 and 38 clamped therein are added to the apparatus with the distractor 11 (FIG. 1) used for the fixation of bone fragments. The braces 35 and 36 are rigidly interconnected by tie bolts 38, defining a rigid system with the needles 37 and 38, said rigid system being attached to the brace 4 by means of two distractors 14 with a system of guides 24 and 25 installed in the midportion thereof. The braces 4 and 35 are interconnected at the top by means of the bending-unbending arrangement 20. The latter type of apparatus permits of a closed correction of the dislocation followed by the restoration of the joint function as well as a closed measured repositioning of the bone fragments to the compression or distraction position.

Figure 8:
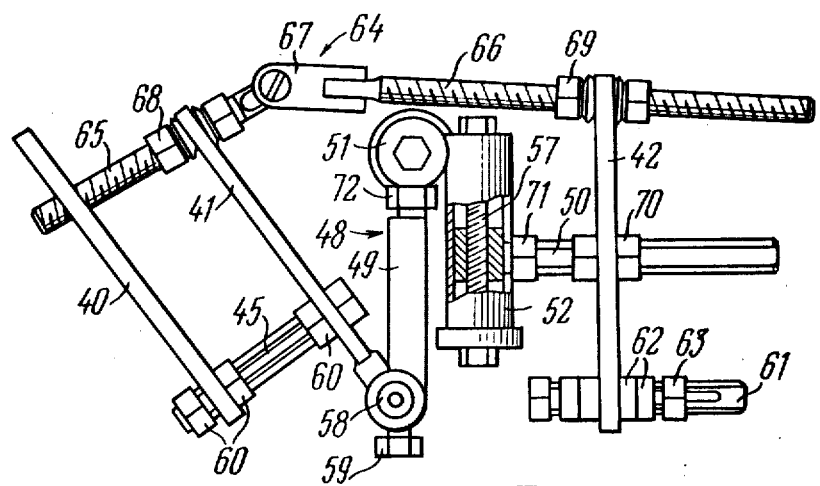
FIG. 8 is a side elevational view, partially cut-away, of an apparatus for surgical treatment of the interphalangeal joints, in accordance with the invention.
Figure 9:
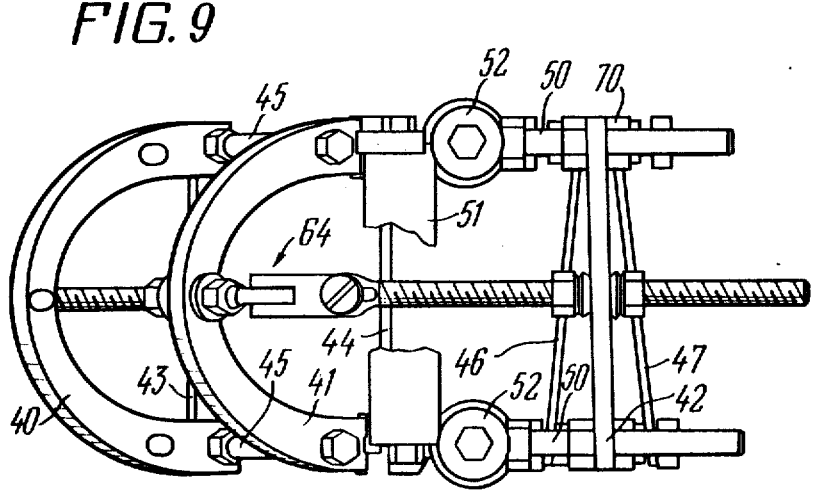
FIG. 9 is a plan view, partially cut-away, of the apparatus shown in FIG. 8.

The proposed apparatus may likewise be employed for treatment of the interphalangeal joints. In such a case the apparatus comprises braces 40, 41 and 42 (FIGS. 8 and 9). A needle 43 (FIG. 9) is clamped in the brace 40, and a needle 44 is clamped in the brace 41, the braces 40 and 41 being rigidly interconnected by fixing screws 45, so that the braces 40 and 41 form a rigid system with the needles 43 and 44. The needles 53 and 44 are designed to be driven through the joint end wherethrough the pivotal axis of the joint passes, i.e. through the distal phalanx, the needle 44 being an axial one which is passed through the pivotal axis of the joint. The other rigid system of the apparatus to be secured on the proximal phalanx comprises the brace 42 with needles 46 and 47 being clamped therein. The two rigid systems are interconnected by two distractors 48 (FIG. 8) each of which comprises two components 49 and 50, with a system of guides 51 and 52 being installed therebetween. The components 49 of the distractors 48 are interconnected by a cross bar 53 (FIG. 10) which forms a frame with the components 49, said frame adding to the rigidity of the apparatus. What with the small size of the apparatus, the guide 51 is common to both distractors 48 (FIG. 8). A slider 54 (FIG. 10) moves in the guide 51. The slider 54 is fastened to the cross bar 51 by means of two screws 55 and cooperates with the drive screw 55 which functions as an antuator of the slider 54. Sliders 56 (FIG. 8) which move in the guides 52 cooperate with drive screws 57, the latter being actuators of said sliders.

The tips of the axial needle 44 (FIG. 9) are secured in the openings of cylindrical hinges 58 (FIG. 8) by means of clamp screws 59. The tips of the needle 43 (FIG. 9) are secured in the notches of the fixing screws 45 by means of nuts 60 (FIG. 8). The tips of the needles 46 and 47 (FIG. 9) of the brace 42 are secured in the notches of fixing screws 61 (FIG. 8) between washers 62 and be means of a nut 63.

The apparatus incorporates a bending-unbending arrangement 64 serving to correct the interphalangeal joint contracture after the dislocated joint has been reduced, and also to restore the joint movement. The bending-unbending arrangement 64 comprises two screws 65 and 66 which are interconnected by a universal joint 67. One end of the bending-unbending arrangment 64 is secured to the top of the brace 41 with the aid of split nuts 68, while the other end is secured to the top of the brace 42 with the aid of split nuts 69.

The distance separating the rigid system defined by the needles 43 and 44 (FIG. 7) and the braces 40 and 41 from the rigid system defined by the needles 46 and 47 and the brace 42 may be increased by use of nuts 70 screwed on the threaded portions 50 of the distractors 48 (FIG. 8).

The slider 56 may be locked with the aid of a nut 71, while the slider 54 (FIG. 10) with the aid of nuts 72.

Figure 11:
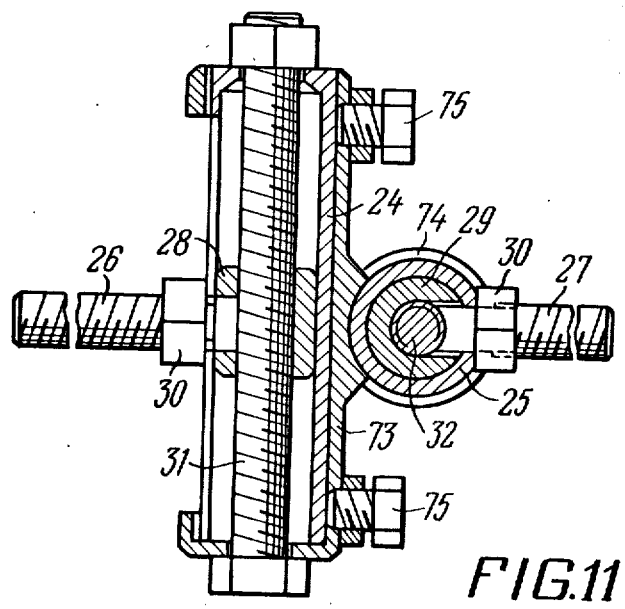
FIG. 11 is a longitudinal sectional view of an alternative embodiment of guides with sliders, in accordance with the invention.

In order to correct an angular displacement of bone fragments, the braces 3 and 4 of the apparatus for surgical treatment of bones shown in FIG. 1 must be installed at a certain angle to the braces 1 and 2. To this end, the guides 24 and 25 as well as the sliders 28 and 29 (FIG. 11) are made round in cross-section and hence capable of rotation; the guides 24 and 25 may be enclosed in casings 73 and 74, respectively, said casings being provided with lock screws 75 which lock the guides 24 and 25 with respect to the casings 73 and 74.

The apparatus for surgical treatment of bones and joints functions as follows.

When the apparatus for surgical treatment of bones shown in FIG. 1 is applied, the needles 7 and 8 are driven through one bone fragment, while the needles 9 and 10 through the other bone fragment, the needles of each pair in one rigid system being installed in angular relationship so as to ensure that the bone fragments or joint ends are securely fixed in the rigid system formed by the needles and the braces.

Then the tips of the needles 7, 8, 9 and 10 are secured in the respective braces 1, 2, 3 and 4, whereupon the boxes 12 with the thread ends of the distractors 11 locked therein are fastened to the braces 2 and 3 by means of screws.

Figure 3:
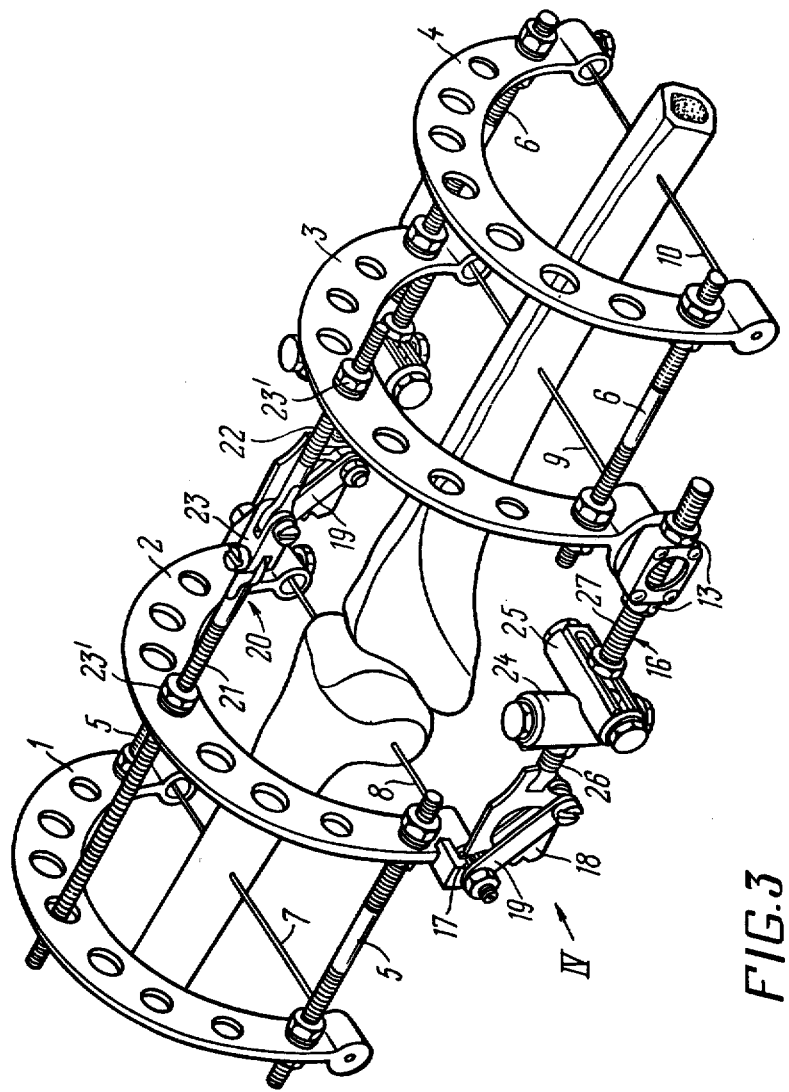
FIG. 3 illustrates an apparatus with distractors for surgical treatment of the knee joint, in accordance with the invention, shown with a knee joint fixed therein.

Application of the apparatus for surgical treatment of joints shown in FIGS. 2 and 3 starts by driving the axial needle 8 through the affected extremity. If the joint surfaces of the elbow-, ankle and radi-carpal joints are unaffected, the axial needle 8 must be aligned with the pivotal axis of the joint end of the bone normally to the main plane of rotation of the joint through the centre of the humeral pulley, through the fulcrum of the wrist and through the centre of the astragalus. When treating the polycentric knee joint which moves by instantaneous displacement of its center of rotation, requiring that the apparatus should employ a polycentric mechanism with a shifting fulcrum which would reproduce the biomechanics of the joint, the axial needle 8 is passed strictly in the main plane of motion of the joint and through those points of the femoral joint end which describe the least curve in the course of flexion and extension. The axial needle 8 is passed at a distance from the articular gap equal to the radius of the joint surface: for elbow joint, this distance is approximately equal to 1.2 cm., i.e. the radius of the capitate eminence; for the angle joint, 2 cm (astragealus radius); for the radio-carpal joint, 1.2 cm (wrist bone radius); and for the knee joint, 2.5 cm (radius of the knee joint pivotal axis when the joint is fully extended).

When the apparatus is applied after the joint surfaces have been prepared, the axial needle 8 must be aligned with the axis of the bone joint end formed as a semicylinder through which passes the pivotal axis of the joint. The axial needle 8 is passed through the eyes of the axial bolts carrying the bearings 15 (FIG. 2) or the gear wheels 17 (FIG. 3) in case of knee joint therapy. Thus, the needle 8 serves as the fulcrum of the apparatus aligned with the pivotal axis of the joint.

After the axial needle 8 has been passed, the needle 7 is driven in the frontal plane through the diaphysis of the bone (FIGS. 2 and 3). Then the needles 9 and 10 are driven through the other joint end. When the apparatus is applied for surgical treatment of fractor dislocations of bones, two more needles, 37 and 38 (FIG. 7), are driven through the distal and proximal fragments, depending on which joint end, distal or proximal, is fractured.

Then the needle tips are secured in the respective braces 1, 2, 3 and 4 (FIGS. 2 and 3) as well as 35 and 36 (FIG. 7), the braces being invariably applied to the extensor-surface of the limb. Then the braces 2 and 3 (FIGS. 2 and 3) and the braces 4 and 35 (FIG. 7) are interconnected by the respective distractors 14 (FIG. 2) or 16 (FIG. 8).

As soon as the apparatus has been applied in an open operation, it is locked by means of the nuts $23^1$ of the bending-unbending arrangement 20 in the median physiological position of the joint for a period of 6 to 7 days, i.e. until the soft tissues have recovered. After this period is over, the joint is subjected to passive and active movement restitution with the aid of the bending-unbending arrangment 20, by displacing its nuts $23^1$, the amplitude of flexion and extension being gradually increased. The method of movement restitution is described hereinbelow. But if the apparatus is applied in a closed manner in the case of contracture, the movement restitution program may be initiated immediately upon application of the apparatus.

If, after the apparatus has been applied, the joint ends or bone fragments are found to be displaced, they must be repositioned. To this end, a lengthwide displacement of the joint ends or bone fragments is corrected with the aid of the split nuts 13 (FIGS. 1, 2, 3 and 7) of the distractors, after which a lateral displacement is corrected by means of the guides 24 and 25 with the sliders 28 and 29 (FIG. 5): as the drive screws 31 are rotated, the bone fragments or joint ends are repositioned in the sagittal plane of the body; whereas rotation of the drive screws 32 causes repositioning in the frontal plane.

The apparatus illustrated in FIG. 1 permits correcting not only a sagittal displacement of the bone fragments but also and simultaneously a rotary displacement thereof. To achieve this, the drive screw 31 (FIG. 5) on the respective side is given a greater extent of travel, the nuts 13 (FIG. 1) being previously slightly loosened, enabling the guides 24 and 25 to be turned about the longitudinal axis of the distractor 11. Thereby it is possible to correct rotary displacements of bone fragments of up to 30° in magnitude.

After the apparatus for treating joints has been applied and the displacement of the joint ends, if any, corrected, a permanent gap 3 to 6 mm in size is established between the joint ends by means of the split nuts 13 (FIGS. 2 and 3) of the distractors. The dislocation having been corrected and the gap between the joint ends established, the joint contracture is eliminated and its mobility restored by means of the bending-unbending arrangement 20. After the bone fragments have been repositioned by the apparatus shown in FIG. 1, the bone fragments are securely fixed in the compression or distraction position.

The apparatus for surgical treatment of fracture dislocations (FIG. 7) is likewise employed for elongating shortened bones, with the nearby joint unloaded by the apparatus retaining its movement. In the course of this procedure, the primry task of the guides 24 and 25 with the sliders consists in maintaining the bone fragments in position while they are being elongated as well as in precisely aligning the bone fragments and fixing them after the bone has been elongated.

After the apparatus has been applied, the joint in the apparatus is fully flexed and extended for 20 or 30 days, by 2° to 6° a day depending on the type of contracture, its duration and the type of joint. After 10 to 15 flexion-extension cycles, the time of flexion and extension is gradually reduced to 15 or 20 minutes, whereupon the bending-unbending arrangement 20 is removed. Over the following 2 or 3 weeks, the patient continues performing active movements with the apparatus staying in position, after which the apparatus is taken off.

While correcting contractures, the apparatus performs a dual function: the variable-lenth distractors are used to proportionately stretch the joint surfaces, obviating their compression; while the bending-unbending arrangment 20 is used to effect a gradual and measured flexion and extention of the joint, the force mounted by the apparatus for eliminating the contracture being distibuted between the joint ends correctly, in accordance with the biomechanical characteristcs of the joint. All these factors are very important for achieving a more phisiological correction of the contracture followed by the restitution of movement of the joint.

The apparatus for surgical treatment of the interphalangeal joints functions as follows. The axial needle 44 (FIG. 9) is driven through the centre of the proximal phalanx head and the tips of the needle 44 are secured in the brace 41. The other needle 43 is driven through the diaphysis of the proximal phalanx 12 to 18 mm proximally with respect to the axial needle 44 and the tips of the needle 43 are secured in the brace 40. Then two needles 46 and 47 are driven through the diaphysis of the distal phalanx and the tips thereof are secured in the brace 42.

Figure 10:
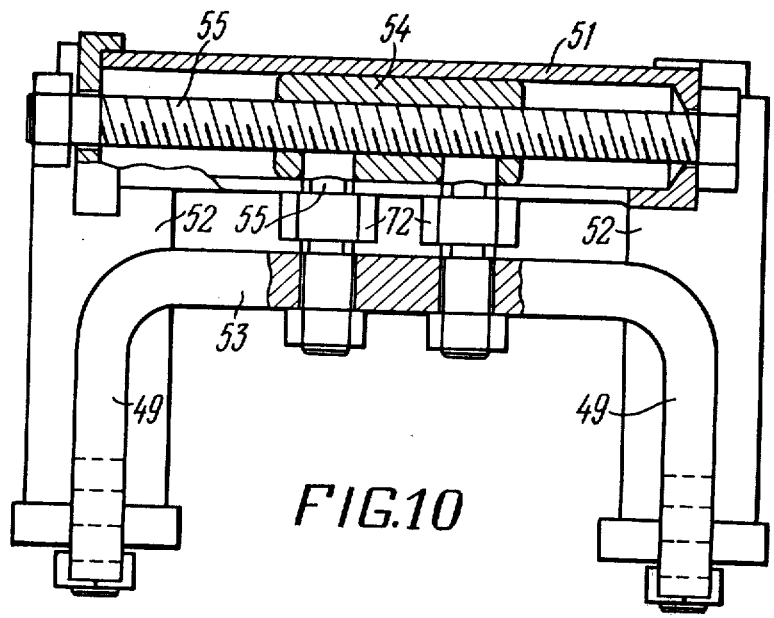
FIG. 10 is a blown-up view, partially in cut-away, of the distractor frame and the common guide of the apparatus shown in FIG. 8.

Lengthwise and angular displacements of the joint ends in the frontal plane of the body are corrected by rotating the nuts 70 of the distractor 48 (FIG. 8): the nuts 70 are rotated equally to correct a lengthwise displacement of the joint ends; if the joint ends are also angularly displaced in the frontal plane, the respective nut 70 is given a longer travel and the distractor 48 on the respective side is lengthened. Lateral and rotary displacements of the joint ends are corrected by moving the sliders 56 and 54 (FIG. 10). Prior to correcting lateral displacements of the joint ends, the nuts 71 and 72 (FIG. 8) are slightly loosened, and as soon as the displacement has been corrected they are retightened. A lateral displacement of the joint ends in the frontal plane of the body is corrected by rotating the drive screw 55 (FIG. 10) which actuates the slider 54. A lateral displacement of the joint ends in the sagittal plane of the body is corrected by simultaneously rotating the drive screws 57 (FIG. 8) which actuate the sliders 56. If a rotary displacement is also the case, the drive screw 57 on the respective sode is given a lower travel, allowing the joint ends to be precisely aligned.

After the joint ends have been precisely aligned, the nuts 70 (FIG. 8) of the distractor 48 are rotated to establish a permanent gap some 2 mm in size between the joint ends, which is required to avoid harmful compression and friction of the joint surfaces.

Rotation of the nuts 68 and 69 of the bending-unbending arrangement 64 results in multiple gradual and measured turns of the brace 42 relative to the braces 40 and 41 and hence the flexion and extension of the joint ends, with the result that the joint contracture is corrected (after the dislocation has been corrected) and the function of the interphalangeal joint is restored.

The apparatus for surgical treatment of the interphalangeal joints is distinguished by virtue of the fact that, instead of two guides disposed laterally with respect to the longitudinal axis of the finger, it comprises one guide 51 with the slider 54 thereof having a far longer travel (FIG. 10) which is used to correct a lateral displacement of the phalanx in the frontal plane; and the phalanx displacement is corrected by rotating one drive screw 55, and not two drive screws, said drive screw 55 being turned with the aid of a single wrench (not shown), largely facilitating the handling of the apparatus. Since the length of the transversal guide 51 disposed above the affected finger is less than the width of the braces, it does not protrude beyond the plane of the apparatus and hence does not interferes with the movements of the adjacent fingers. With the short components 49 of the distractors being incorporated in a single frame, the apparatus is capable of fixing the joint ends much more securely.

What is claimed is:

1. An apparatus for surgical treatment of bones and joints comprising: at least two pairs of needles designed to be driven through the juxtaposed bones; at least two braces, the tips of said needles of one of said pairs of needles being secured in each said brace so that said brace forms a rigid system with said needles, said rigid system being designed to be secured on the respective bone being juxtaposed; two distractors interconnecting said rigid systems, each said distractor being formed as a split member composed of two roughly equal components; each component of said distractor having one end thereof attached to said brace of said rigid system and having a second end; a slider fastened to said second end of said distractor component; two interconnected guides, said slider of one of said distractor components moving along one of said guides; said guides disposed in perpendicular relationship one with the other and also with the longitudinal axes of said distractor components connected therewith by way of said sliders; screw actuators for propelling said sliders along said guides.

2. An apparatus as set forth in claim 1, wherein said sliders and said guides are round in cross-section and thus capable of executing a rotary motion relative to each other.

3. An apparatus as set forth in claim 1, wherein said distractors are so secured to said braces of said rigid systems as to be able to execute a fixed turn about the axies thereof.

4. An apparatus as set forth in claim 2, wherein said distractors are so attached to said braces of said rigid systems as to be able to execute a fixed turn about the axes thereof.

5. An apparatus as set forth in claim 1, wherein said distractors are so attached to said braces of said rigid systems as to be able to execute a fixed turn about the axes thereof.

* * * * *